United States Patent [19]
Rottenberg et al.

[11] Patent Number: 5,735,882
[45] Date of Patent: Apr. 7, 1998

[54] CARDIAC STIMULATOR WITH BACKUP-MODE SELF-RECOVERY

[75] Inventors: William B. Rottenberg; Patrick J. Paul; David Prutchi, all of Lake Jackson, Tex.

[73] Assignee: Sulzer Intermedics Inc., Angleton, Tex.

[21] Appl. No.: 755,699

[22] Filed: Nov. 25, 1996

[51] Int. Cl.$^6$ ...................................................... A61N 1/37
[52] U.S. Cl. ........................................................... 607/27
[58] Field of Search .................................. 607/27, 29, 63

[56] References Cited

U.S. PATENT DOCUMENTS

| | | |
|---|---|---|
| 3,618,615 | 11/1971 | Grestbatch . |
| 3,920,024 | 11/1975 | Bowers . |
| 4,344,437 | 8/1982 | Markowitz . |
| 4,485,818 | 12/1984 | Leckrone et al. . |
| 5,413,592 | 5/1995 | Schroeppel ................. 607/18 |
| 5,456,692 | 10/1995 | Smith, Jr. et al. ............ 607/31 |
| 5,480,414 | 1/1996 | Stroebel et al. ............. 607/28 |
| 5,607,458 | 3/1997 | Causey et al. ............... 607/27 |

OTHER PUBLICATIONS

Intermedics Cardiac Pulse Generator Physician's Manual.

*Primary Examiner*—Scott M. Getzow
*Attorney, Agent, or Firm*—John R. Merkling

[57] ABSTRACT

A cardiac stimulator with a method and apparatus for automatically switching the cardiac stimulator to its normal mode from its backup mode. A fault monitor receives fault signals and determines whether a particular fault warrants activation of the backup mode. If so, a number of attempts to reactivate the normal mode are permitted. The normal mode may be reactivated if the stored information is valid and if the circuitry is operational.

21 Claims, 6 Drawing Sheets

CARDIAC STIMULATOR WITH BACKUP-MODE SELF-RECOVERY

BACKGROUND OF THE INVENTION

1. Field of the Invention

The present invention relates generally cardiac stimulators and, more particularly, to cardiac stimulators having backup modes.

2. Description of the Related Art

As most people are aware, the human heart is an organ having four chambers. A septum divides the heart in half, with each half having two chambers. The upper chambers are referred to as the left and right atria, and the lower chambers are referred to as the left and right ventricles. Deoxygenated or impure blood enters the right atrium through the pulmonary veins. Contraction of the right atrium and of the right ventricle pump the deoxygenated blood through the pulmonary arteries to the lungs where the blood is oxygenated or purified. This oxygenated blood is carried to the left atrium by the pulmonary veins. From this cavity, the oxygenated blood passes to the left ventricle and is pumped to a large artery, the aorta, which delivers the pure blood to the other portions of the body through the various branches of the vascular system.

For a variety of reasons, a person's heart may not function properly and, thus, endanger the person's well-being. Medical devices have been developed to facilitate heart function. For instance, if a person's heart does not beat properly, a cardiac stimulator may be used to provide relief. A cardiac stimulator is a medical device that delivers electrical stimulation to a patient's heart. A cardiac stimulator generally includes a pulse generator for creating electrical stimulation pulses and a conductive lead for delivering these electrical stimulation pulses to the designated portion of the heart.

Cardiac stimulators generally fall into two categories, pacemakers and defibrillators, although some cardiac stimulators may perform both functions. Pacemakers supply electrical pulses to the heart to keep the heart beating at a desired rate. Defibrillators supply a relatively larger electrical pulse to the heart to help the heart recover from cardiac failure.

Early pacemakers did not monitor the condition of the heart. Rather, early pacemakers simply provided stimulation pulses at a fixed rate and, thus, kept the heart beating at that fixed rate. However, it was found that pacemakers of this type used an inordinate amount of energy because the stimulation pulses were not always needed. In fact, the human heart includes a sinus node located above the right atrium. The sinus node provides the electrical stimulation that causes a heart to contract. Even the sinus node of a heart in need of a pacemaker often provides such stimulation. Accordingly, if a heart, even for a short period, is able to beat on its own, providing an electrical stimulation pulse using a pacemaker wastes the pacemaker's energy.

To conserve power, pacemakers were subsequently designed to monitor the heart and to provide stimulation pulses only when necessary. These pacemakers were referred to as "demand" pacemakers because they provided stimulation only when the heart demanded stimulation. If a demand pacemaker detected a natural heartbeat within a prescribed period of time, typically referred to as the "escape interval", the pacemaker provided no stimulation pulse. Because monitoring uses much less power than generating stimulation pulses, the demand pacemakers took a large step toward conserving the limited energy contained in the pacemaker's battery.

Clearly, the evolution of the pacemaker did not cease with the advent of monitoring capability. Indeed, the complexity of pacemakers has continued to increase in order to address the physiological needs of patients as well as the efficiency, longevity, and reliability of the pacemaker. For instance, even the early demand pacemakers provided stimulation pulses, when needed, at a fixed rate, such as 70 pulses per minute. To provide a more physiological response, pacemakers having a programmably selectable rate were developed. So long as the heart was beating above this programmably selected rate, the pacemaker did not provide any stimulation pulses. However, if the heart rate fell below this programmably selected rate, the pacemaker sensed the condition and provided stimulation pulses as appropriate.

In addition to programmable rate pacemakers, pacemakers were developed that generated stimulation pulses having lower energy levels to conserve power. Pacemakers of this type, not only monitored the heart to determine whether it was beating on its own in the absence of stimulation pulses, it also monitored the heart to determine whether it was beating properly in response to these lower energy stimulation pulses.

Another major step in adding complexity and functionality to pacemakers occurred with the advent of pacemakers that had dual chamber capability. Dual chamber pacemakers are capable of sensing and/or pacing in two chambers, typically the right atrium and right ventricle. Accordingly, the distal ends of an atrial lead and a ventricular lead are coupled to the dual chamber pacemaker. The proximal end of the atrial lead is threaded through the superior vena cava and into the right atrium of the heart. Similarly, the proximal end of the ventricular lead is threaded through the superior vena cava, through the right atrium, and into the right ventricle of the heart. Each lead includes a mechanism on its proximal end that attaches to the inner wall of the heart to establish the required electrical connection between the pacemaker and the heart. Dual chamber pacemakers, as compared to single chamber pacemakers, typically function in a more physiologically correct manner and, thus, conserve more power.

To provide even further physiological accuracy, pacemakers have now been developed that automatically change the rate at which the pacemaker provides stimulation pulses. These pacemakers are commonly referred to as "rate-responsive" pacemakers. Rate-responsive pacemakers sense a physiological parameter of the patient (or a parameter correlative to the level of activity of the patient) and alter the rate at which the stimulation pulses are provided to the heart. Typically, this monitored physiological parameter relates to the changing physiological needs of the patient. For instance, when a person is at rest, the person's heart may beat relatively slowly to accommodate the person's physiological needs. Conversely, when a person is exercising, the person's heart tends to beat rather quickly to accommodate the person's heightened physiological needs. Unfortunately, the heart of a person in need of a pacemaker may not be able to beat faster on its own. In fact, prior to the development of rate-responsive pacemakers, patients were typically advised to avoid undue exercise, and pacemaker patient's that engaged in exercise tended to tire quickly.

Rate-adaptive pacemakers help relieve this problem by sensing one or more physiological parameters of a patient that indicates whether the heart should be beating slower or faster. If the pacemaker determines that the heart should be beating faster, the pacemaker adjusts its base rate upward to provide a faster pacing rate if the patient's heart is unable to beat faster on its own. Similarly, if the pacemaker determines that the patient's heart should be beating more slowly, the pacemaker adjusts its base rate downward to conserve energy and to conform the patient's heartbeat with the patient's less active state.

As can be seen from the previous discussion, pacemakers have evolved into quite complex devices. In fact, current pacemakers may be programmed into a variety of different modes that vary in complexity. Currently, the most complex operational mode is DDDR, while the least complex operational mode is V00. It should be noted that the earliest pacemakers operated in V00 mode. In other words, as previously described, the earliest pacemakers only provided stimulation pulses to the ventricle, and did not include any monitoring or rate-responsive capabilities. Similarly, many current pacemakers are capable of operating in DDDR mode.

These acronyms are deciphered as follows. The first position indicates where pacing takes place, and the second position indicates where sensing takes place. Therefore, a D indicates that the pacemaker is operating in a dual mode, while A indicates that the function takes place only in the atrium and V indicates that the function takes place only in the ventricle. The third position indicates whether the pacemaker is operating in triggered mode, inhibited mode, or both, using the letters T, I, and D, respectively. Finally, the fourth position indicates whether the pacemaker is rate-responsive, using the presence or absence of the letter R.

As can be appreciated, as pacemakers have become more complex, the electronic circuitry used to implement the pacemaker's functions has also become more complex. In fact, most pacemakers currently employ a microprocessor that controls much of the complex functionality of the pacemaker. The microprocessor, of course, operates under the control of a program that is typically stored in read only memory (ROM). The microprocessor also receives information from the various sensors and other operational circuitry associated with the pacemaker. Much of this information is stored in random access memory (RAM) for the microprocessor's use.

Given the complexity of a current pacemaker's circuitry and the number of parameters sensed and adjusted by the pacemaker, it is not surprising that certain circumstances may exist that cause the pacemaker to malfunction. Therefore, pacemakers may monitor themselves and generate a fault signal if a possible malfunction is detected. If a fault condition exists, a pacemaker operating in a complex mode may revert to a less complex mode, typically referred to as the backup mode. A more complex mode, such as DDDR, is typically programmed into a pacemaker to provide more physiologically accurate functioning and more efficient operation. However, if a fault condition exists, the pacemaker defaults into the backup mode in which the pacemaker operates in a less efficient and less complex fashion, but still maintains the pacing functions. Accordingly, the pacemaker uses more power and operates in a manner less adaptive to physiological changes in the patient.

By way of example, a pacemaker programmed to operate in the DDDR mode may default into a VVI backup mode in response to the pacemaker determining that a fault condition may exist. Because the VVI mode is a simpler mode that relies on fewer variables and, thus, less complex portions of the pacemaker's circuitry, it typically proves to be a more reliable mode of insuring that the patient's heart is paced is an adequate manner even if the fault condition was caused by the failure of a portion of the pacemaker's circuitry. In addition, the energy contained in the stimulation pulses used in the backup mode is typically sufficient to ensure contraction of the heart muscle under virtually any situation, as contrasted with a more complex mode where lower energy stimulation pulses are used to conserve power. Of course, the backup mode may be an even less complex mode, such as V00. As previously described, in V00 mode, the pacemaker delivers stimulation pulses to the ventricle at a fixed rate without relying on monitoring or any other parameters. Although the V00 mode may severely limit the activity in which the patient may engage, it will keep the patient's heart beating to permit the patient to visit his physician.

Current pacemakers do not contain self diagnostics that permit the pacemaker to return to its normal programmed mode after it has defaulted into its backup mode. As a result, a patient whose pacemaker has switched from its normal programmed mode to the backup mode must visit their physician who reprograms the pacemaker to cause the pacemaker to operate in a normal programmed mode rather than the backup mode. Thus, until a physician reprograms the pacemaker, it uses more energy than necessary and, hence, shortens the life of the pacemaker. Also, until the pacemaker is reprogrammed, the patient's activities may be curtailed because the pacemaker is operating in a less physiologically accurate mode.

The present invention is directed to overcoming, or at least reducing the effects of, one or more of the problems set forth above.

SUMMARY OF THE INVENTION

In accordance with one aspect of the present invention, there is provided a cardiac stimulator that is operable in a normal mode and in a backup mode. The cardiac stimulator includes a circuit for generating a fault signal in response to detecting a fault condition in the normal mode. A fault monitor is coupled to the circuit to receive the fault signal, and the fault monitor activates the backup mode. A recovery circuit is operable in the backup mode, and the recovery circuit reactivates the normal mode.

In accordance with another aspect of the present invention, there is provided a cardiac stimulator that is automatically switchable from a normal operational mode to a backup operational mode. The improvement includes a means for automatically switching the cardiac stimulator from the backup operational mode to the normal operational mode.

In accordance with a further aspect of the present invention, there is provided a cardiac stimulator that is operable in a normal mode and in a backup mode. The cardiac stimulator includes a plurality of circuits that are operational in the normal mode. Each of these circuits generates a respective fault signal in response to detecting a fault condition during operation in the normal mode. A fault monitor is coupled to the plurality of circuits to receive the respective fault signals. The fault monitor categorizes each received fault signal as a hard fault signal or as a soft fault signal. The fault monitor activates the backup mode in response to a received fault signal being categorized as a hard fault signal. A recovery circuit is operable in the backup mode, and the recovery circuit automatically reactivates the normal mode.

In accordance with yet another aspect of the present invention, there is provided a cardiac stimulator that is operable in a normal mode and in a backup mode. The cardiac stimulator includes a pulse generator that is operable in the normal mode and in the backup mode. The pulse generator produces normal stimulation pulses in the normal mode and backup stimulation pulses in the backup mode. A plurality of circuits are operational in the normal mode. Each of these circuits generates a respective fault signal in response to detecting a fault condition during operation in the normal mode. A fault monitor is coupled to the plurality of circuits to receive the respective fault signals. The fault monitor activates the backup mode in response to a received fault signal meeting a given criterion. A recovery circuit is operable in the backup mode, and the recovery circuit automatically reactivates the normal mode.

In accordance with still another aspect of the present invention, there is provided a cardiac stimulator that is operable in a normal mode and a backup mode. The cardiac stimulator includes a plurality of circuits that are operational in the normal mode. Each of these circuits generates a respective fault signal in response to detecting a fault condition during operation in the normal mode. A fault monitor is coupled to the plurality of circuits to receive the respective fault signals. The fault monitor categorizes each received fault signal as a hard fault signal or as a soft fault signal. The fault monitor activates the backup mode in response to a received fault signal being categorized as a hard fault signal. A recovery circuit is operable in the backup mode. The recovery circuit tests at least the circuit that generated the hard fault signal. The recovery circuit automatically reactivates the normal mode in response to the test meeting a given criterion.

In response to a still further aspect of the present invention, there is provided a method for automatically returning a cardiac stimulator to a normal mode of operation from a backup mode of operation. The method includes the steps of: (a) determining whether selected memory locations contain valid information; (b) determining whether selected circuitry is operational; and (c) generating a signal to reactivate the normal mode.

In accordance with a yet further aspect of the present invention, there is provided a method for automatically returning a cardiac stimulator to a normal mode of operation from a backup mode of operation. The method comprises the steps of: (a) storing information correlative to activation of the backup mode; (b) determining if a given number of recoveries have been attempted; (c) if a given number of recoveries have not been attempted, determining whether selected memory locations contain valid information; (d) if the selected memory locations contain valid information, determining whether programmed parameters correlative to the normal mode are valid; (e) if the programmed parameters are valid, determining whether selected critical circuitry is operational; (f) if the selected critical circuitry is operational, determining whether selected non-critical circuitry is operational; (g) if the selected non-critical circuitry is not operational, determining whether rerouting can avoid the non-operational non-critical circuitry; and (h) if the selected non-critical circuitry is operational or if rerouting can avoid the non-operational non-critical circuitry, generating a signal to reactivate the normal mode.

In accordance with an even further aspect of the present invention, there is provided an apparatus for automatically returning a cardiac stimulator to a normal mode of operation from a backup mode of operation. The apparatus includes means for determining whether selected memory locations contain valid information, means for determining whether selected circuitry is operational, and means for generating a signal to reactivate the normal mode.

In accordance with an even still further aspect of the present invention, there is provided an apparatus for auto- matically returning a cardiac stimulator to a normal mode of operation from a backup mode of operation. The apparatus includes means for storing information correlative to activation of the backup mode, means for determining if a given number of recoveries have been attempted, means for determining whether selected memory locations contain valid information, means for determining whether programmed parameters correlative to the normal mode are valid, means for determining whether selected critical circuitry is operational, means for determining whether selected non-critical circuitry is operational, and means for generating a signal to reactivate the normal mode.

BRIEF DESCRIPTION OF THE DRAWINGS

The foregoing and other advantages of the invention will become apparent upon reading the following detailed description and upon reference to the drawings in which.

DESCRIPTION OF SPECIFIC EMBODIMENTS

Figure 1:
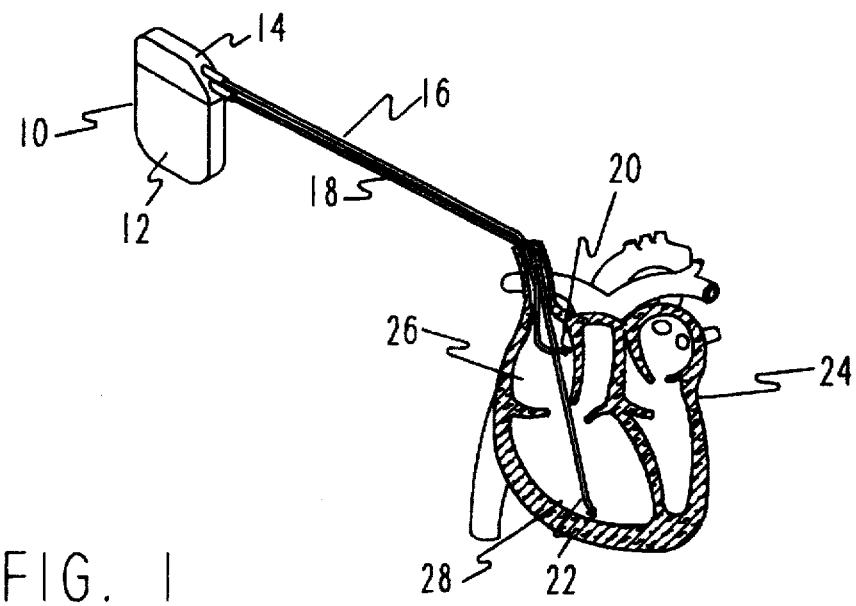
FIG. 1 illustrates a pacemaker having two leads coupled to a patient's heart.

Turning now to the drawings and referring initially to FIG. 1, one embodiment of a cardiac pacemaker is illustrated and generally designated by a reference numeral 10. The pacemaker 10 includes a backup mode self recovery apparatus that will be described in detail herein. If the pacemaker 10 detects a circumstance that may cause the pacemaker 10 to switch from its normal programmed mode into its backup mode, the backup mode self recovery apparatus may attempt to deal with the circumstance without reverting to backup mode, or it may attempt to return the pacemaker 10 to its normal programmed mode of operation after its has reverted to its backup mode.

The body of the pacemaker 10 is made up of a case 12 and a header 14. The pacemaker 10 may be implantable or non-implantable. If implantable, the case 12 and the header 14 are hermetically sealed to prevent bodily fluids from damaging the internal circuitry of the pacemaker 10. Typically, the case 12 is made of titanium, and the header 14 is made of epoxy.

In the described embodiment, the pacemaker 10 is a dual chamber pacemaker, although it should be understood that the teachings set forth herein may apply to other types of pacemakers, including single chamber pacemakers. Because the pacemaker 10 is a dual chamber pacemaker, it includes an atrial lead 16 and a ventricular lead 18. Typically, the leads 16 and 18 are generally flexible and include an electrically conductive core surrounded by a protective sheath. For instance, the internal core may be a coiled titanium wire, and the protective sheath may be a coating of polyurethane. Each lead 16 and 18 includes a respective tip 20 and 22 that is designed to be implanted and coupled to an interior surface of a chamber of the heart 24. As illustrated, the tip 20 of the atrial lead 16 is implanted in an inner wall of the right atrium 26 of the heart 24 for sensing and/or stimulating the right atrium 26. Similarly, the tip 22 of the ventricular lead 18 is implanted in an inner wall of the right ventricle 28 of the heart 24 for sensing and/or stimulating the right ventricle 28.

Figure 2:
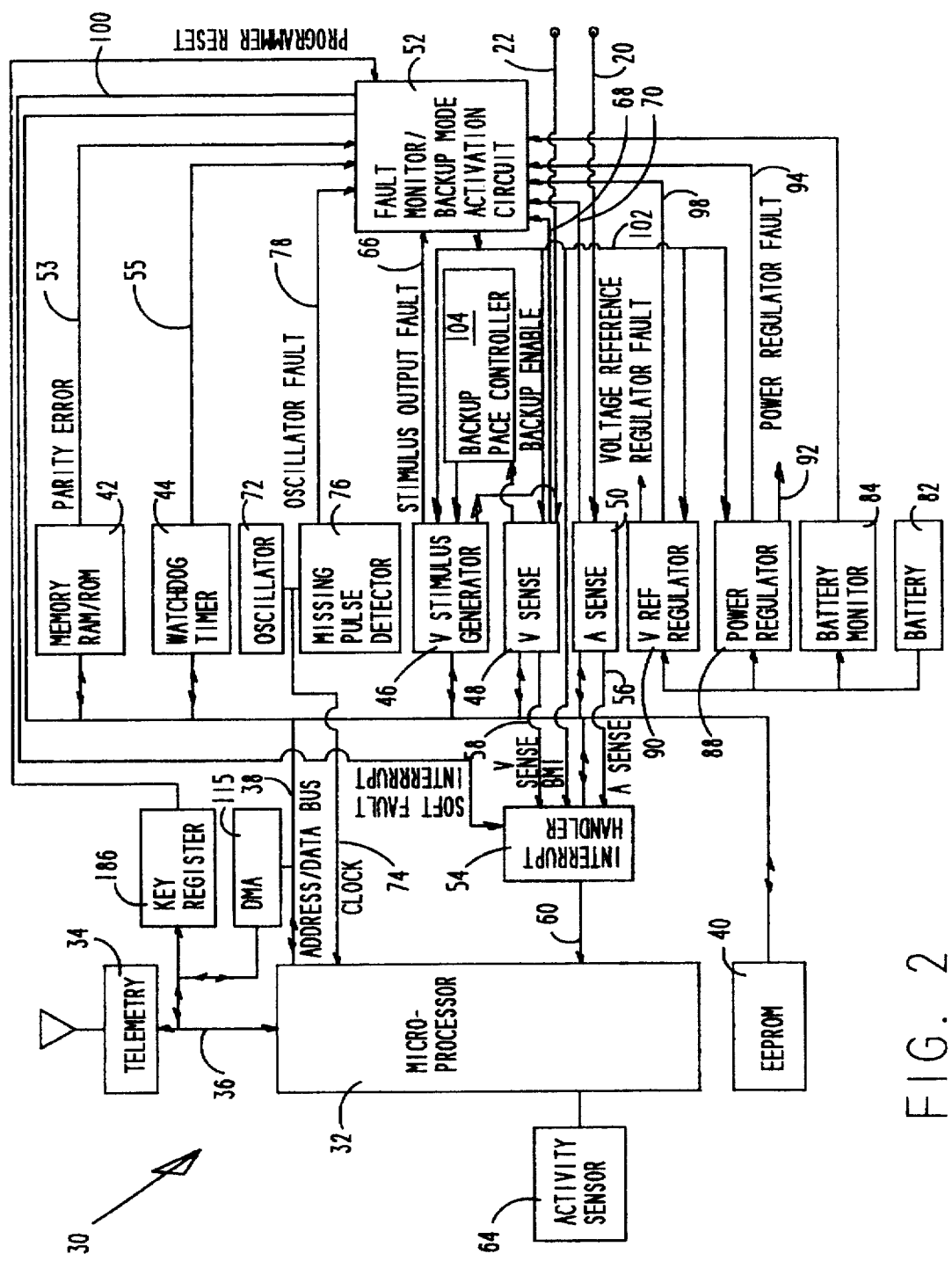
FIG. 2 illustrates a block diagram of one embodiment of a pacemaker's circuitry in accordance with the present invention.

The pacemaker 10 uses electronic circuitry to perform its functions, such as the circuitry illustrated in FIG. 2 and generally designated by the reference numeral 30. The circuitry 30 includes a microprocessor 32 that controls many functions of the pacemaker 10. A telemetry circuit 34 facilitates communication between the pacemaker 10 and a programmer (not shown) located external to the patient's body. Using the programmer, a physician may program various parameters into the circuitry 30 to tailor the pacemaker's functionality to a patient's particular situation. The telemetry circuitry 34 is coupled to the microprocessor 32 via a bus 36.

To control the functions of the pacemaker 10, the microprocessor 32 is coupled to a variety of other circuits via an address/data bus 38. In this embodiment, for instance, the address/data bus 38 couples the microprocessor 32 to a non-volatile memory, such as the electrically erasable programmable read only memory (EEPROM) 40, a main memory 42, a watchdog timer 44, a ventricular stimulus generator 46, a ventricular sense circuit 48, an atrial sense circuit 50, a fault monitor and backup mode activation circuit 52, and an interrupt handler 54. Each of these subcircuits will be discussed in greater detail below.

The EEPROM 40, in this embodiment, is advantageously used to store parameters programmed into the pacemaker 10 by a physician. The EEPROM 40 may also be used to store other programs and parameters used by the microprocessor 32. As will be described in detail below, the EEPROM 40 is used to store programs and parameters relating to a backup mode self recovery feature of the pacemaker 10.

The main memory 42 typically contains random access memory (RAM) and read only memory (ROM). The ROM stores the primary operating programs and parameters used by the microprocessor 32 to perform the functions of the pacemaker 10. The RAM typically stores parameters and portions of programs currently being used by the microprocessor 32 during operation of the pacemaker 10. Additionally, in certain embodiments, the RAM portion of the main memory 42 may be used to store parameters programmed by a physician.

The main memory 42 includes a parity checking circuit (not shown) that ensures that data being read from the memory are valid, uncorrupted data. Typical parity checking schemes use a parity bit, in addition to the data bits, which is either set or not set to provide the correct parity if the data are valid. In this embodiment, odd parity is used, i.e., if the number of ones in the data and parity bits adds up to an odd number, the data are valid.

A number of circumstances may exist that may cause the parity to be incorrect or the data to be invalid. For instance, a power fluctuation could corrupt data stored in the main memory 42. Such a power fluctuation might be caused by, for example, a power supply transient, or a strong electromagnetic noise source, such as electrosurgery. Regardless of the circumstance producing the parity error, once the parity checking circuit of the main memory 42 detects the error, it delivers a parity error signal on line 53 to the fault monitor and backup mode activation circuit 52.

The watchdog timer 44 periodically monitors the microprocessor 32 to ensure that the microprocessor 32 is functioning properly. If the microprocessor 32 is operating properly, it periodically polls the watchdog timer 44. Every time the watchdog timer 44 is polled, its timer resets and begins counting again until the next time the microprocessor 32 polls the watchdog timer 44. If the microprocessor 32 does not poll the watchdog timer 44 within the prescribed period of time, the watchdog timer 44 delivers a processor fault signal on line 55 to the fault monitor and backup mode activation circuit 52 to indicate that the microprocessor 32 may not be functioning properly.

The pacemaker 10 may stimulate the heart 24 in both the atrium 26 and the ventricle 28. However, for ease of illustration, only the ventricular stimulus generator 46 is illustrated in FIG. 2, with the understanding that comments regarding the ventricular stimulus generator 46 similarly apply to an atrial stimulus generator used in the pacemaker 10. The atrial lead 20 delivers information on the electrical condition of the atrium 26 to the atrial sense circuit 50. Similarly, the ventricular lead 22 delivers information on the electrical condition of the ventricle 28 to the ventricular sense circuit 48. The atrial sense circuit 50 and the ventricular sense circuit 48 deliver this information to an interrupt handler 54 via lines 56 and 58, respectively. The interrupt handler 54 passes this information to the microprocessor 32 via line 60.

Based, in part, on the information delivered to it by the atrial sense circuit 50 and the ventricular sense circuit 48, the microprocessor 32 controls the timing of the ventricular stimulus generator 46. Of course, the microprocessor 32 may base its control of the ventricular stimulus generator 46 on other parameters, such as information received from other sensors. For example, an activity sensor 64, such as an implanted accelerometer, may be used to gather information relating to changing levels of patient activity.

If an error is detected in the stimulating or sensing functions performed by the ventricular stimulus generator 46, the ventricular sense circuit 48, or the atrial sense circuit 50, an appropriate fault signal is delivered to the fault monitor and backup mode activation circuit 52. For instance, the stimulation pulse delivered by the ventricular stimulus generator 46 may be improper for some reason. Possible examples may include improper pulse timing, such as runaway pulses, insufficient amplitude, or insufficient duration. Once such a fault is detected, the ventricular stimulus generator 46 delivers a stimulus output fault on line 66 to the fault monitor and backup mode activation circuit 52.

Similarly, a fault may arise in the sensing function of the pacemaker 10. By way of example, it is possible that a fault may occur in the circuitry of the ventricular sense circuit 48 or the atrial sense circuit 50. In this case, accurate information regarding the electrical condition of the heart 24 may not be delivered to the microprocessor 32. Accordingly, once a fault of this type is detected, a ventricular sense fault or an atrial sense fault is delivered via lines 68 and 70, respectively, to the fault monitor and backup mode activation circuit 52.

In addition to the circuits previously discussed, the pacemaker 10 may include other circuitry whose condition is monitored to detect the occurrence of a fault condition. As a first example, the pacemaker 10 includes an oscillator 72. The oscillator 72 provides the main clock signal to the microprocessor 32 via line 74. It is possible that the clock signal provided by the oscillator 72 may deteriorate in some fashion. The oscillator 72 may malfunction in some manner that affects the timing, duration, or amplitude of the clock signals delivered onto line 74. For instance, the oscillator 72 may miss or skip pulses. Alternatively, an external noise source might cause the deterioration of clock signals delivered to the microprocessor 32. Accordingly, a fault detector, such as a missing pulse detector 76, is coupled to the oscillator 72. If the missing pulse detector 76 detects missing or distorted clock pulses, it delivers an oscillator fault signal on line 78 to the fault monitor and backup mode activation circuit 52.

The pacemaker 10 also includes a power circuit, which is generally designated by a reference numeral 80. The pacemaker 10 includes a battery 82 that provides power to the pacemaker's circuitry. As stated previously, power conservation is one primary concern behind pacemaker design and operation. The longer that the battery 82 is able to power the pacemaker 10 adequately, the longer the pacemaker 10 may remain implanted in a patient. Accordingly, the condition of the battery 82, and of the other components of the power circuit 80, are adjusted and monitored to ensure the accurate and adequate delivery of power to the pacemaker's circuitry.

A battery monitor 84 is coupled to the battery 82. The battery monitor 84 monitors the output voltage, and possibly the resistance of, the battery 82. Typically, the output voltage and the resistance of the battery 82 will change over time. If the output voltage of the battery 82 drops too low, it may affect the operation of the pacemaker's circuitry, including the delivery of stimulation pulses to the heart 24. Also, external noise sources, such as electrosurgery, can drop the battery voltage below that needed to power certain portions of the pacemaker's circuitry, such as the RAM. If the RAM loses power, any data stored within the RAM is lost. Because the microprocessor 32 relies on the programs and data stored in the RAM, it may be unable to function properly unless and until these programs and data are restored. Accordingly, when the battery monitor 84 detects that the battery voltage has dropped below a certain level, it delivers a battery fault signal on line 86 to the fault monitor and back up mode activation circuit 52.

The power circuit 80 also includes two regulators—a power regulator 88 and a voltage reference regulator 90. The power regulator 88 provides a regulated voltage signal on line 92 to power other portions of the pacemaker's circuitry. If the regulated voltage provided by the power regulator 88 dips too low, it may not adequately power the pacemaker's circuitry and, thus, the circuitry may not function as intended. Although the power regulator 88 typically includes circuitry that adjusts for changes in the voltage and resistance of the battery 82, circumstances might exist that would cause an undesirable output from the power regulator 88. External noise sources, as described above, are one example of a cause of such a disruption. If a fault is detected, the power regulator 88 delivers a power regulator fault signal on line 94 to the fault monitor and backup mode activation circuit 52.

The voltage reference regulator 90 delivers a voltage reference signal on line 96 to other circuits of the pacemaker 10 that use a reference voltage. The reference voltage may be quite important to certain of the pacemaker's circuits to ensure that they function properly. For instance, the ventricular sense circuit 48 and the atrial sense circuit 50 may use a reference voltage to determine the existence of a ventricular sense event and an atrial sense event, respectively, or to sense the adequacy of a stimulation pulse generated by the ventricular stimulus generator 46. If the reference voltage supplied on line 96 varies outside of a certain tolerance range, the circuits that use the reference voltage may not function as intended. Low battery voltage, external noise sources, or deterioration of the reference components may cause such a variance in the voltage reference signal supplied on line 96. Accordingly, if it is determined that the voltage reference signal is faulty for some reason, a voltage reference regulator fault is delivered on line 98 to the fault monitor and backup mode activation circuit 52.

The fault monitor and backup mode activation circuit 52 receives the fault signals from the various portions of the circuit 30 and determines whether to send the pacemaker 10 into backup mode. The fault monitor and backup mode activation circuit 52 may simply activate the backup mode in response to any received fault signal. However, because each fault signal denotes a different type of circumstance, each fault signal may be dealt with differently. Accordingly, the fault monitor and backup mode activation circuit 52 may treat each fault differently, with some faults causing initiation of the backup mode and other faults not causing such initiation.

The fault monitor and backup mode activation circuit 52, in one embodiment, separates the faults into "soft" faults and "hard" faults. Generally speaking, soft faults may be a category of faults that may be cured without switching the pacemaker 10 from its normal mode of operation into its backup mode of operation. Likewise, hard faults may be a category of faults that may not be cured until after the pacemaker 10 is switched from its normal mode of operation into its backup mode of operation. If the fault monitor and backup mode activation circuit 52 determines that one of the previously described fault signals should be categorized as a soft fault, it delivers a soft fault interrupt signal on line 100 to the interrupt handler 54. Once the microprocessor 32 reads the soft fault interrupt signal from the interrupt handler 54, it attempts to cure the fault without switching the pacemaker 10 into backup mode. For example, a parity error detected in the main memory 42 may be one example of a soft fault that may be cured without switching the pacemaker 10 into its backup mode.

If the fault monitor and backup mode activation circuit 52 determines that one of the previously described fault signals should be categorized as a hard fault, it delivers a hard fault signal (which may also be referred to as a backup enable signal or a backup mode interrupt signal) on line 102 to a number of different circuits. For instance, the hard fault signal is delivered to a backup pace controller 104, the ventricular stimulus generator 46, the ventricular sense circuit 48, the atrial sense circuit 50, the interrupt handler 54, the power regulator 88, and the voltage reference regulator 90. The purpose of delivering the hard fault signal to each of these circuits is discussed below.

The backup pace controller 104, in this embodiment, is a state machine that functions independently of the microprocessor 32. Therefore, even if the microprocessor 32 is inoperable, the pacemaker 10, under control of the backup pace controller 104, will continue to provide stimulation pulses to the heart 24. Although the stimulation pulses generated in the normal mode of operation may have very low amplitudes, e.g., under 2.5 volts, and relatively narrow pulse widths, e.g., under 0.3 milliseconds, the backup pace controller 104 typically generates stimulation pulses having more energy than those used during the normal mode. For instance, the backup pace controller 104 may generate stimulation pulses having amplitudes of 5.4 volts and pulse widths of 0.5 milliseconds. Furthermore, although the pacemaker 10 may provide variable rate pulse timing in its normal mode, the backup pace controller 104 generally provides fixed pulsed timing, such as 70 beats per minute.

In this embodiment, the backup pace controller 104 generally operates in the VVI mode, which means that it paces the ventricle and is inhibited by intrinsic activity detected in the ventricle. However, because the sensitivity of the ventricular sensing in the backup mode may be quite low to avoid false inhibition due to noise, the backup pace controller 104 may be operating virtually in a V00 mode.

Once the backup pace controller 104 has taken over the pacing functions of the pacemaker 10, other circuitry within the pacemaker 10 is informed that operation has switched into the backup mode. For instance, the fault monitor and backup mode activation circuit 52 delivers a backup mode interrupt signal to the interrupt handler 54. When the microprocessor 32 receives the backup mode interrupt signal from the interrupt handler 54, the microprocessor 32 halts its pacing routines. The microprocessor 32 may also initiate a self-recovery attempt, as will be described in detail later with reference to FIGS. 4–7.

The fault monitor and backup mode activation circuit 52 also delivers backup enable signals on line 102 to the ventricular stimulus generator 46, the ventricular sense circuit 48, the atrial sense circuit 50, the power regulator 88, and the voltage reference regulator 90. Each of these circuits may use different parameters depending upon whether the pacemaker 10 is operating in its normal mode or its backup mode, because, typically, the parameters used in the backup mode result in the pacemaker providing more conservative and less efficient pacing functions as compared with the parameters used during the normal mode of operation. Accordingly, each of these circuits may include a normal mode/backup mode parameter selection circuit.

Figure 3:
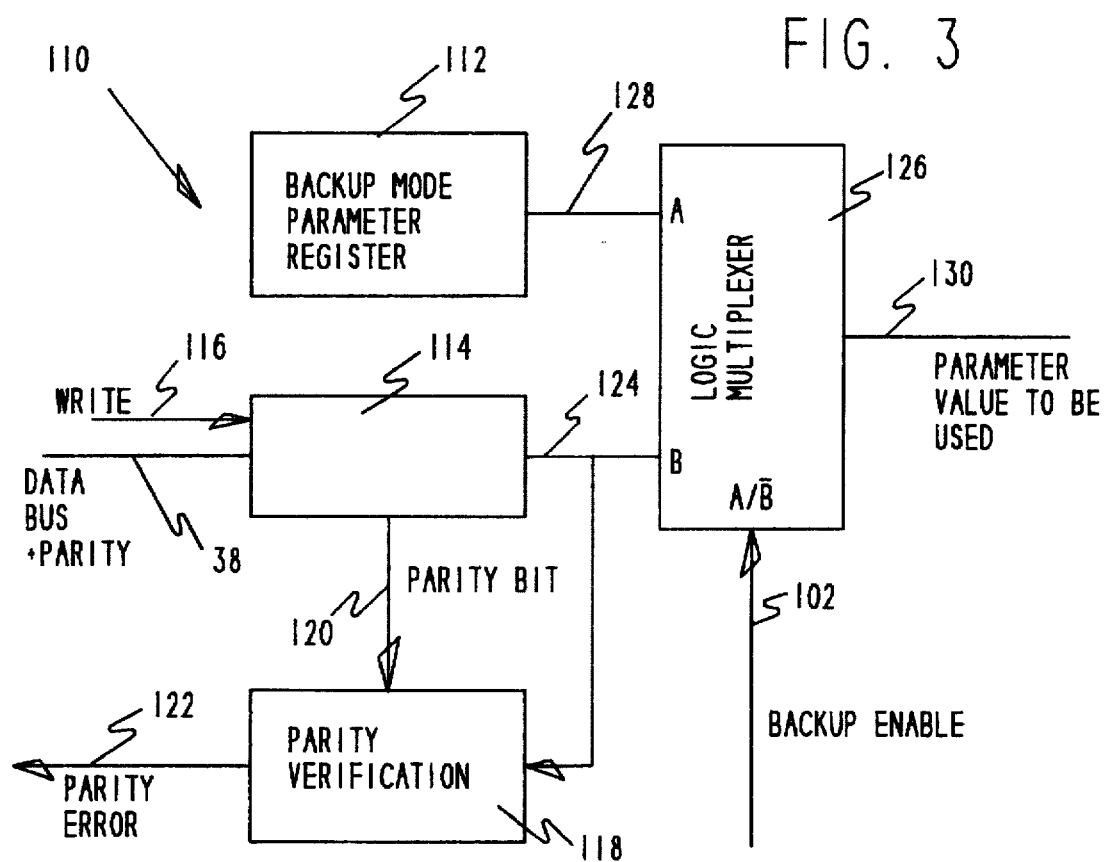
FIG. 3 illustrates a block diagram of normal/backup mode circuitry used by various subcircuits illustrated in FIG. 2.

One embodiment of such a parameter selection circuit is illustrated in FIG. 3 and generally designated by a reference numeral 110. The parameter selection circuit 110 includes a backup mode parameter register 112 that stores a backup-mode parameter. In this embodiment, the register 112 is hard-wired or otherwise permanently programmed with the backup mode parameter. The parameter selection circuit 110 also includes a normal mode parameter register 114. The normal mode parameter register 114 may store data and parity information delivered to it by the microprocessor 32, or by the telemetry circuit 34 by way of the Direct Memory Access controller (DMA) 115, via the data bus 38. The microprocessor 32 initiates storage of information in the normal mode parameter register 114 by delivering a write signal to it via line 116. The normal mode parameter register 114 delivers its parity bit to a parity verification circuit 118 via line 120. If the parity verification circuit 118 determines that a parity error exists, it delivers a parity error signal on line 122 to the microprocessor 32 or to the fault monitor and backup mode activation circuit 52. However, assuming that the normal mode parameter register 114 contains valid data, the normal mode parameter register 114 delivers the data on a bus 124 to the B input of a logic multiplexer 126. Similarly, the backup mode parameter register 112 delivers its data on a bus 128 to the A input of the logic multiplexer 126.

Of course, the parameters stored in the parameter registers of each subcircuit are typically different. The parameter registers in the ventricular stimulus generator 46 store parameters indicating the amplitude and pulse width for the stimulation pulses. In the ventricular sense circuit 48 and the atrial sense circuit 50, the parameter registers store the amplitude of the R wave and of the P wave, respectively, that would trigger the respective sense circuit. In the power regulator 88 and the voltage reference regulator 90, the parameter registers may store parameters for optimizing the respective outputs of the power regulator 88 and the voltage reference regulator 90. For instance, the normal mode parameter registers 114 may, from time to time, receive new configurations from the microprocessor 32. These parameters may be delivered by the microprocessor 32 due to changes in the battery voltage or impedance in order to improve the efficiency of the pacemaker 10. The backup mode parameter registers 112 in the power regulator 88 and the voltage reference regulator 90 may store more conservative parameters as compared to the normal mode, or they may store parameters that indicate that the power from the battery 82 should be used directly by the pacemaker's circuitry in backup mode with no regulation.

During the normal mode of operation, the backup enable signal delivered to the logic multiplexer 126 on line 102 is low. Accordingly, the logic multiplexer 126 outputs the data from the normal mode parameter register 114 onto a bus 130. However, once the logic multiplexer 126 receives the backup enable signal on line 102, it outputs the data from the backup mode parameter register 112 onto the bus 130. Therefore, even if the microprocessor 132 continues to deliver parameters into the normal mode of parameter register 114, the ventricular stimulus generator 46, the ventricular sense circuit 48, the atrial sense circuit 50, the power regulator 88, and the voltage reference regulator 90 ignore these programmed parameters. Instead, these circuits use the backup mode parameter stored in their respective backup mode parameter registers 112.

Figure 4:
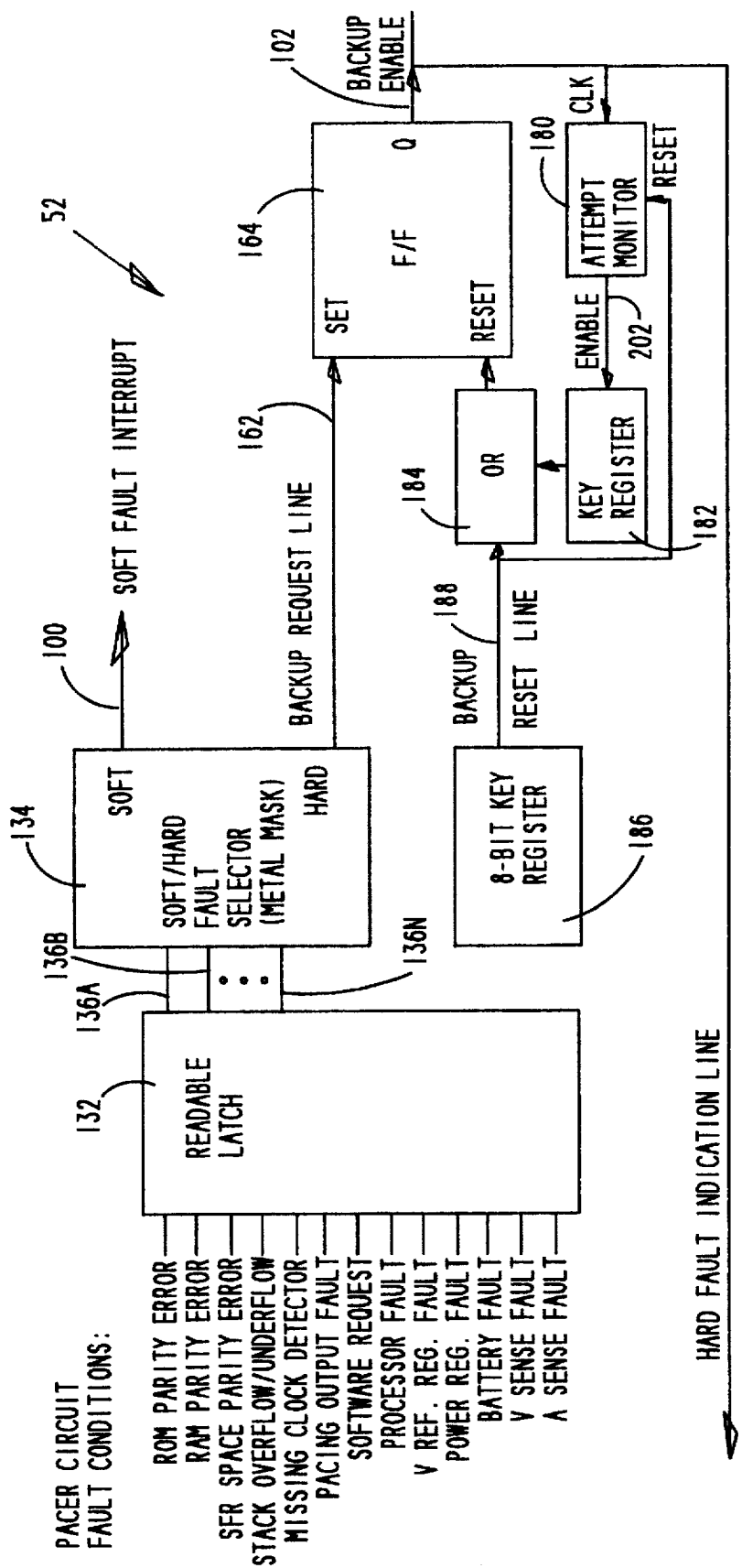
FIG. 4 illustrates a block diagram of one embodiment of fault monitor and backup mode recovery circuitry in accordance with the present invention.

The basic components of this embodiment of the fault monitor and the backup mode activation circuit 52 are illustrated in FIG. 4. The various fault signals that may be generated by the various subcircuits of the pacemaker 10 are delivered to a readable latch 132. The latch 132 temporarily stores the state of the fault signals delivered to it. A soft/hard fault selector 134 reads the temporarily stored fault signals from the latch 132. The fault selector 134 contains decoding logic that permits it to determine whether a particular fault signal should be placed in the category of soft fault or in the category of hard fault. In this embodiment, the fault selector 134 is a mask programmable read only memory. As such, it may be formed on the same chip as the microprocessor 32 and other portions of the pacemaker's circuitry.

Figure 5:
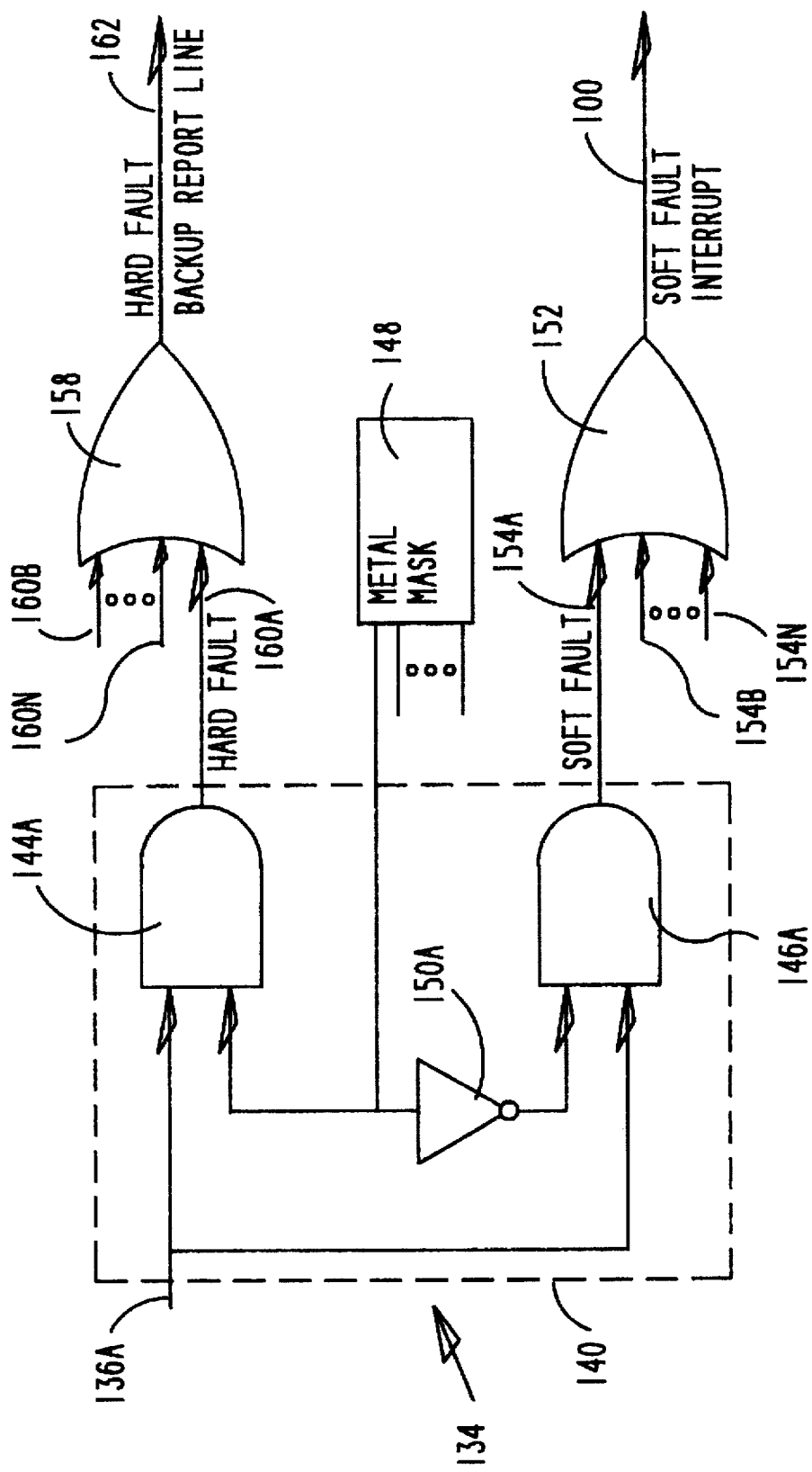
FIG. 5 illustrates a logic diagram of one embodiment of the soft/hard fault selector illustrated in FIG. 4.

FIG. 5 illustrates a logical diagram of circuitry that may be used to implement the fault selector 134. Each input from the latch 132 on a line 136A–136N is processed by a similar logic circuit 140. For ease of illustration, only one such circuit is shown with the understanding that a separate logic circuit 140 is used with each input line 136A–136N. The input on line 136A is delivered to two AND gates 144A and 146A. The AND gates 144A and 146A receive another input signal related to the selected programmed state for each particular fault signal. In this embodiment, the selected states are programmed in a metal mask 148. The metal mask 148 delivers its logic signal directly to the AND gate 144A. However, the logic signal from the metal mask 148 is inverted by an inverter 150A before it is delivered to the AND gate 146A. Accordingly, the selected state delivered from the metal mask 148 will enable one AND gate and disable the other AND gate depending upon whether the particular fault condition received on line 136A should be categorized as a hard fault or a soft fault.

By way of example, a RAM parity error may be categorized as a soft fault. If the RAM parity error signal is delivered to the fault selector 134 on line 136A, the metal mask 148 outputs a logical zero, which disables the hard fault AND gate 144A and enables the soft fault AND gate 146A. Accordingly, the soft fault AND gate 146A outputs a logical one. An OR gate 152 is coupled to the output of each soft fault AND gate 146A-N. The OR gate 152 receives this logical one signal from the soft fault AND gate 146A on line 154A. Accordingly, the OR gate 152 generates a logical one soft fault interrupt signal on line 100. The soft fault interrupt on line 100 is delivered to the interrupt handler 54 and to the microprocessor 32, as previously described in reference to FIG. 2.

Let us now assume that the fault signal delivered on line 136A should be characterized as a hard fault. For instance, the metal mask 148 may be programmed to categorize a watchdog fault signal as a hard fault. Accordingly, if line 136A in FIG. 5 delivers the watchdog fault signal to the fault selector 134, the metal mask 148 delivers a logical one signal to the hard fault AND gate 144A and a logical zero signal to the soft fault AND gate 146A. Thus, the hard fault AND gate 144A delivers a logical one signal to an OR gate 158 on a line 160A. The OR gate 158 also receives signals from other AND gates 144B-144N on lines 160B-160N. If any of the inputs to the hard fault OR gate 158 are logical one, the hard fault OR gate 158 generates a logical one hard fault signal on a line 162.

Referring again to FIG. 4, the hard fault signal on the backup request line 162 is delivered to the set input of a flip-flop such as the set/reset flip-flop 164. If the flip-flop 164 receives a logical one at its set input, the flip-flop 164 outputs a backup enable signal on line 102. As previously described with reference to FIG. 2, line 102 delivers the backup enable signal to a number of different circuits within the pacemaker 10. In particular, the backup enable signal acts as a backup mode interrupt signal and is delivered to the microprocessor 32 via the interrupt handler 54.

Figure 6:
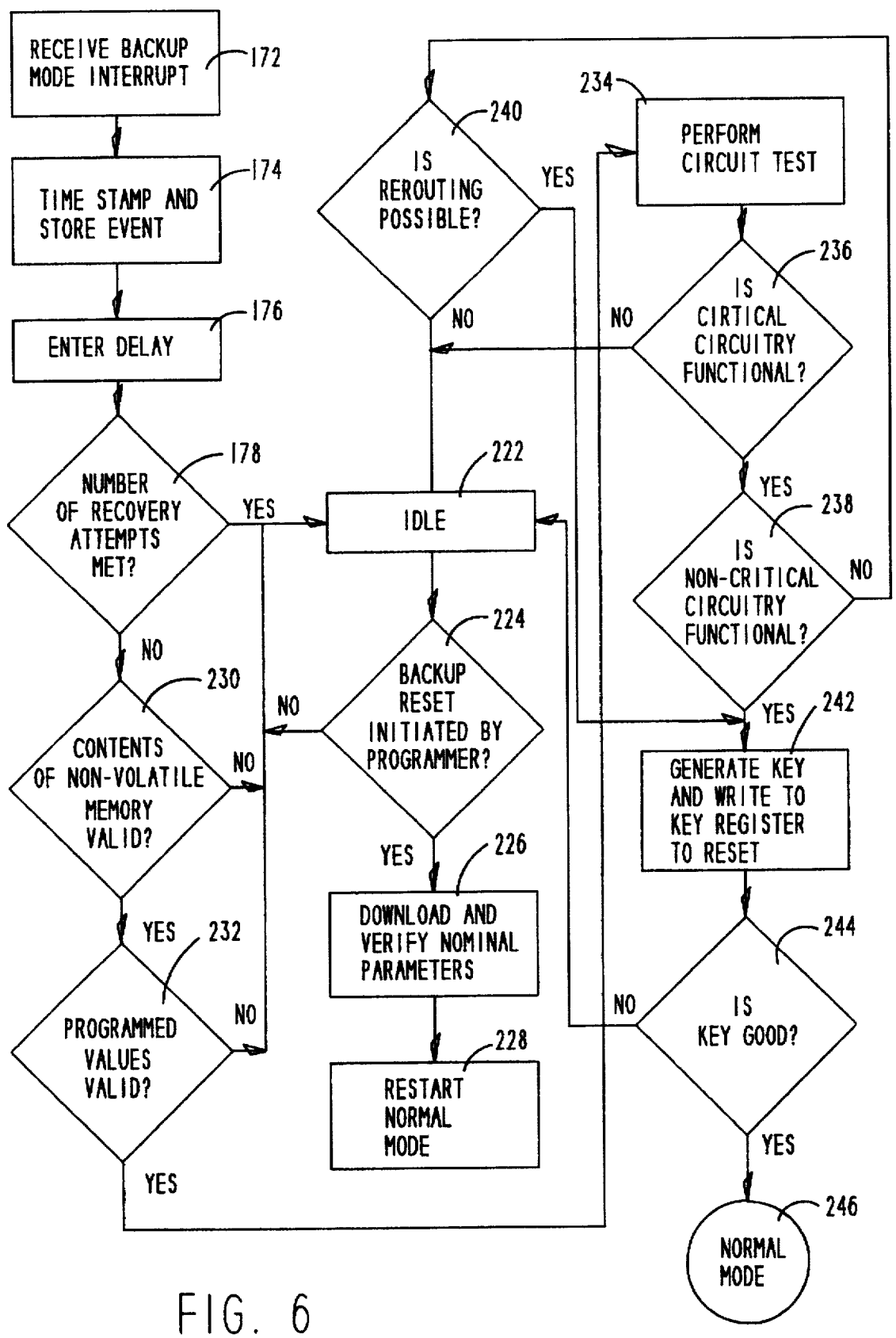
FIG. 6 illustrates a flowchart depicting a program and method, used in conjunction with the circuitry illustrated in FIG. 4, to facilitate recovery of a pacemaker from backup mode to normal mode.

The actions taken by the microprocessor 32 in response to receiving a backup mode interrupt signal are described below with reference to the flowchart 170 illustrated in FIG. 6. The microprocessor 32 first determines that it has received a backup mode interrupt signal (block 172). Once the microprocessor 32 has been notified that the pacemaker 10 is entering backup mode, it time stamps and stores the event in registers within the microprocessor or in a protected area of RAM (block 174). The microprocessor 32 then enters a delay (block 176), which may be about 30 seconds for instance. This delay allows potential causes of interference, e.g., electrosurgery, to disappear before self-recovery from the backup mode is attempted. The length of this delay may vary depending upon the type of fault detected. Once this delay is over, the microprocessor 32 is vectored to a backup mode routine that may enable the pacemaker 10 to reset itself under control of the microprocessor 32, so that the pacemaker 10 can reenter its normal mode of operation.

In this embodiment, the microprocessor 32 first attempts to determine whether the number of allowed recovery attempts has been met before it attempts to recover from backup mode (block 178). To facilitate this function, the fault monitor and backup mode activation circuit 52 includes an attempt monitor 180, as illustrated in FIG. 4. The attempt monitor 180 receives each backup enable signal generated by the flip-flop 164. As long as the number of received backup enable signals is less than a predetermined number of allowed self-recovery attempts, the attempt monitor 180 delivers an enable signal to a key register circuit 182. As described below with further reference to FIGS. 6 and 7, the key register circuit 182 receives a key written to it by the microprocessor 32 during a self recovery attempt. If the self recovery attempt succeeds, the key register circuit 182 delivers a self recovery backup reset signal to an OR gate 184. The OR gate 184, in turn, delivers a backup reset signal to the reset input of the flip-flop 164. Upon receiving a reset signal, the flip-flop 164 ceases to deliver the backup enable signal.

The pacemaker 10 can also be returned to normal mode from backup mode by a programmer. As illustrated in FIGS. 2 and 4, a programmer may enter a key into a key register 186. The key register 186 delivers a programmer-mediated backup reset signal to the OR gate 184 on line 188. The OR gate 184 in turn delivers a backup reset signal to the flip-flop signal 164 to disable the backup enable signal.

Figure 7:
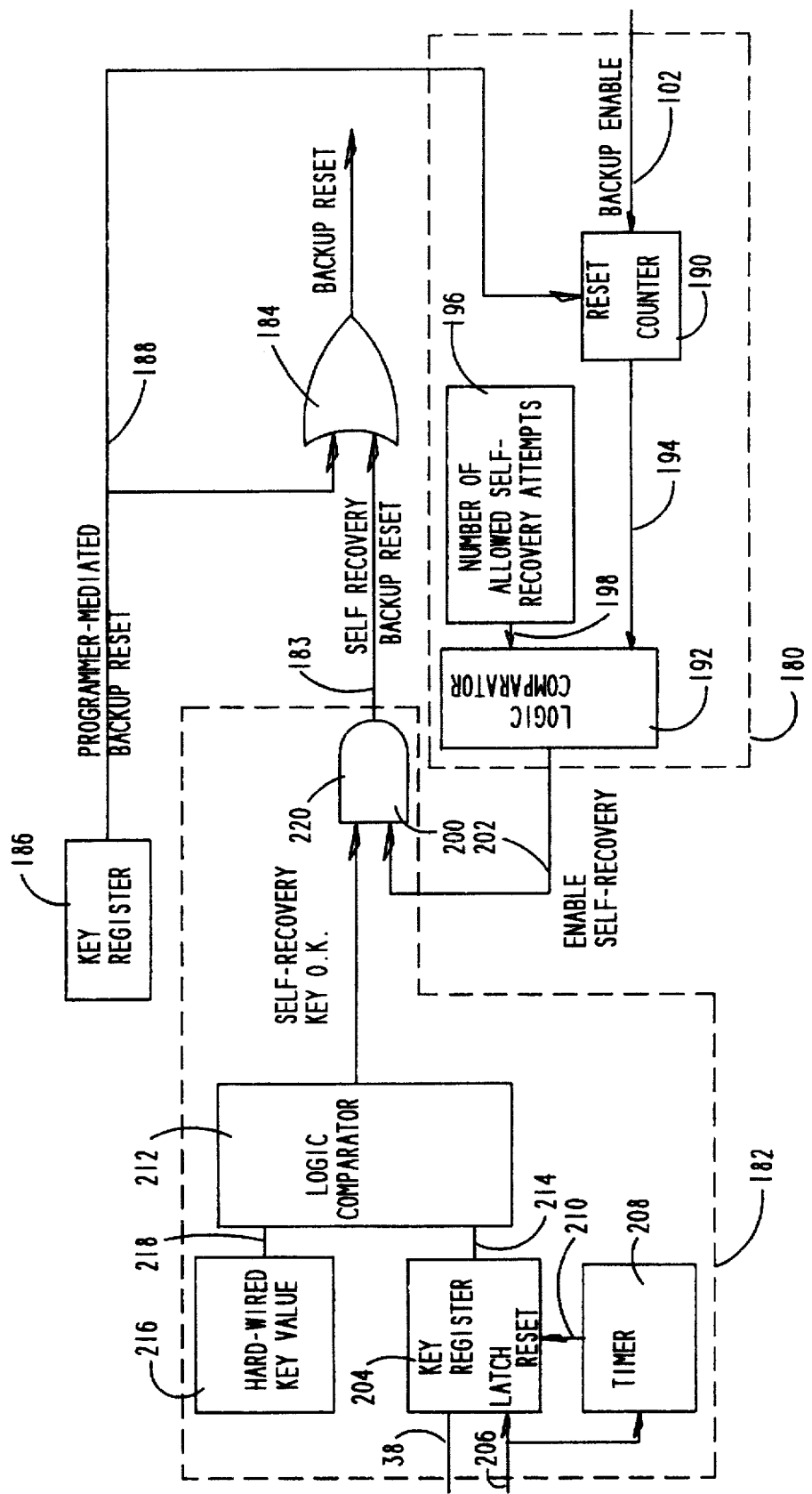
FIG. 7 illustrates a logic diagram of one embodiment of the attempt monitor and key register circuit illustrated in FIG. 4.

One embodiment of the attempt monitor 180 in the key register circuit 182 is illustrated in FIG. 7. The attempt monitor 180 includes a counter 190 that receives the backup enable signal on line 102. The counter 190 delivers its count to a logic comparator 192 via a bus 194. The logic comparator 192 also receives a programmed count from a programmed counter 196 via a bus 198. The programmed counter 196 may be mask programmable or it may be a reprogrammable logic circuit. If the number of allowed self recovery attempts from the programmed counter 196 is greater than the number of actual self recovery attempts from the counter 190, the logic comparator 192 delivers a self recovery enable signal to an AND gate 200 on line 202.

Still referring to FIG. 7, the key register circuit 182 includes a key register 204 that is coupled to the data bus 38, so that the microprocessor 32 can write a key into the key register 204 by delivering a write signal on line 206. A timer 208 is reset by the write signal on line 206. Once the timer 208 times out, it delivers a reset signal on line 210 to the key register 204. The reset signal clears the key register 204 after a predetermined period of time so that unintentional self-recovery from the backup mode does not occur in case the pacemaker returns to the backup mode after a self-recovery attempt. The key register 204 delivers its key to a logic comparator 212 via a bus 214. A preprogrammed key register 216 also delivers its key to the logic comparator 212 via a bus 218. If the key programmed by the microprocessor contained in the key register 204 is the same as the preprogrammed key contained in the key register 216, the logic comparator 212 delivers a self recovery key OK signal to the AND gate 200 on line 220. Thus, if the AND gate 200 is enabled, it delivers a self recovery backup reset signal on line 183 to the OR gate 184.

Referring again to FIG. 6, if the number of permitted recovery attempts has been met, the microprocessor 32 switches into an idle mode (block 222) until a backup request is initiated by a programmer, as described previously with respect to FIGS. 4 and 7. Once a backup reset has been initiated by the programmer (block 224), the microprocessor downloads and verifies the nominal parameters (block 226). Then, the microprocessor 32 is vectored to restart its normal mode of operation (block 228).

If the number of recovery attempts has not been met, the microprocessor 32 determines whether the contents of the non-volatile memory, e.g., the EEPROM 40, are valid (block 230). If the contents are not valid, the microprocessor 32 switches into an idle state (block 222). If the contents are valid, the microprocessor 32 downloads the last programmed parameters to determine if they are valid (block 232). If these last programmed values are not valid, the microprocessor 32 switches into the idle state (block 222). If the last programmed values are valid, the microprocessor performs a circuit test (block 234).

The circuitry may be categorized as critical circuitry and non-critical circuitry. If the critical circuitry is not functional (block 236), the microprocessor 32 switches into the idle state (block 222). If the critical circuitry is functional, the microprocessor 32 determines whether the non-critical circuitry is functional (block 238). If the non-critical circuitry is not functional, the microprocessor determines whether the non-functional circuitry can be avoided by rerouting or eliminating certain non-critical functions (block 240). If not, the microprocessor 32 enters the idle state (block 222). If the non-critical circuitry is functional, or if the non-functional circuitry can be avoided, the microprocessor 32 generates a key and writes the key to the key register 204 to reset the pacemaker 10 from backup mode into normal mode (block 242). If the key register circuit 182 determines that the key is good, the pacemaker 10 returns to normal mode (block 244). If not, then the microprocessor 32 enters the idle state (block 222).

It should be noted that the number or recovery attempts need not be monitored. Instead, the pacemaker 10 may attempt an unlimited number of recovery attempts, or the attempts may be limited by time rather than number. However, it is generally undesirable to switch the pacemaker 10 repeatedly between the normal mode and the backup mode. If the pacemaker 10 does not stay in its normal mode after a certain number of recovery attempts, or after a certain period of time, it may be assumed that the fault is one from which the pacemaker 10 cannot recover.

Specific embodiments of the invention have been shown by way of example in the drawings and have been described in detail herein. However, the invention may be susceptible to various modifications and alternative forms, and it should be understood that the invention is not intended to be limited to the particular forms disclosed. Rather, the invention is to cover all modifications, equivalents, and alternatives falling within the spirit and scope of the invention as defined by the appended claims.

What is claimed is:

1. A cardiac stimulator being operable in a normal mode and in a backup mode, said cardiac stimulator comprising:
    a circuit for generating a fault signal in response to detecting a fault condition in said normal mode;
    a fault monitor being coupled to said circuit to receive said fault signal, said fault monitor activating said backup mode; and
    a recovery circuit operable in said backup mode, said recovery circuit automatically reactivating said normal mode.

2. The cardiac stimulator, as set forth in claim 1, wherein said fault monitor activates said backup mode in response to a received fault signal meeting a given criterion.

3. The cardiac stimulator, as set forth in claim 1, wherein said recovery circuit tests said circuit that generated said fault signal, said recovery circuit automatically reactivating said normal mode in response to said test meeting a given criterion.

4. The cardiac stimulator, as set forth in claim 1, further comprising:
    a pulse generator being operable in said normal mode and in said backup mode, said pulse generator producing normal stimulation pulses in said normal mode and producing backup stimulation pulses in said backup mode.

5. In a cardiac stimulator being automatically switchable from a normal operational mode to a backup operational mode, said improvement comprising:
    means for automatically switching said cardiac stimulator from said backup operational mode to said normal operational mode.

6. The cardiac stimulator, as set forth in claim 5, wherein said means comprises:
    a fault monitor being coupled to a plurality of circuits to receive respective fault signals, said fault monitor activating said backup mode in response to a received fault signal meeting a given criterion; and
    a recovery circuit operable in said backup mode, said recovery circuit automatically reactivating said normal mode.

7. The cardiac stimulator, as set forth in claim 5, wherein said means comprises:
    means for determining whether selected memory locations contain valid information;
    means for determining whether selected circuitry is operational; and
    means for generating a signal to reactivate said normal mode.

8. The cardiac stimulator, as set forth in claim 5, further comprising:
    a pulse generator being operable in said normal mode and in said backup mode, said pulse generator producing normal stimulation pulses in said normal mode and producing backup stimulation pulses in said backup mode.

9. A cardiac stimulator being operable in a normal mode and in a backup mode, said cardiac stimulator comprising:
    a plurality of circuits being operational in said normal mode, each of said plurality of circuits generating a respective fault signal in response to detecting a fault condition during operation in said normal mode;
    a fault monitor being coupled to said plurality of circuits to receive said respective fault signals, said fault monitor categorizing each received fault signal as one of a hard fault signal and a soft fault signal, said fault monitor activating said backup mode in response to a received fault signal being categorized as a hard fault signal; and
    a recovery circuit operable in said backup mode, said recovery circuit automatically reactivating said normal mode.

10. The cardiac stimulator, as set forth in claim 9, wherein said recovery circuit tests said circuit that generated said fault signal, said recovery circuit automatically reactivating said normal mode in response to said test meeting a given criterion.

11. The cardiac stimulator, as set forth in claim 9, further comprising:
    a pulse generator being operable in said normal mode and in said backup mode, said pulse generator producing normal stimulation pulses in said normal mode and producing backup stimulation pulses in said backup mode.

12. A cardiac stimulator being operable in a normal mode and in a backup mode, said cardiac stimulator comprising:
    a pulse generator being operable in said normal mode and in said backup mode, said pulse generator producing normal stimulation pulses in said normal mode and producing backup stimulation pulses in said backup mode;
    a plurality of circuits being operational in said normal mode, each of said plurality of circuits generating a respective fault signal in response to detecting a fault condition during operation in said normal mode;

a fault monitor being coupled to said plurality of circuits to receive said respective fault signals, said fault monitor activating said backup mode in response to a received fault signal meeting a given criterion; and a recovery circuit operable in said backup mode, said recovery circuit automatically reactivating said normal mode.

13. The cardiac stimulator, as set forth in claim 12, wherein said fault monitor categorizes each received fault signal as one of a hard fault signal and a soft fault signal, said fault monitor activating said backup mode in response to a received fault signal being categorized as a hard fault signal.

14. The cardiac stimulator, as set forth in claim 12, wherein said recovery circuit tests at least said circuit of said plurality of circuits that generated said hard fault signal, said recovery circuit automatically reactivating said normal mode in response to said test meeting a given criterion.

15. A cardiac stimulator being operable in a normal mode and in a backup mode, said cardiac stimulator comprising:

a plurality of circuits being operational in said normal mode, each of said plurality of circuits generating a respective fault signal in response to detecting a fault condition during operation in said normal mode:

a fault monitor being coupled to said plurality of circuits to receive said respective fault signals, said fault monitor categorizing each received fault signal as one of a hard fault signal and a soft fault signal, said fault monitor activating said backup mode in response to a received fault signal being categorized as a hard fault signal; and a recovery circuit operable in said backup mode, said recovery circuit testing at least said circuit of said plurality of circuits that generated said hard fault signal, and said recovery circuit automatically reactivating said normal mode in response to said test meeting a given criterion.

16. A method for returning a cardiac stimulator to a normal mode of operation from a backup mode of operation, said method comprising the steps of:

(a) determining whether selected memory locations contain valid information;

(b) determining whether selected circuitry is operational; and (c) automatically generating a signal to reactivate said normal mode.

17. The method, as set forth in claim 16, wherein step (a) comprises the step of:

determining whether programmed parameters correlative to said normal mode are valid.

18. The method, as set forth in claim 16, wherein step (b) comprises the steps of:

determining whether selected critical circuitry is operational;

determining whether selected non-critical circuitry is operational; and if said selected non-critical circuitry is not operational, determining whether rerouting can avoid said non-operational non-critical circuitry.

19. A method for automatically returning a cardiac stimulator to a normal mode of operation from a backup mode of operation, said method comprising the steps of:

(a) storing information correlative to activation of said backup mode;

(b) determining if a given number of recoveries have been attempted;

(c) if said given number of recoveries have not been attempted, determining whether selected memory locations contain valid information;

(d) if said selected memory locations contain valid information, determining whether programmed parameters correlative to said normal mode are valid;

(e) if said programmed parameters are valid, determining whether selected critical circuitry is operational;

(f) if said selected critical circuitry is operational, determining whether selected non-critical circuitry is operational;

(g) if said selected non-critical circuitry is not operational, determining whether rerouting can avoid said non-operational non-critical circuitry; and (h) if said selected non-critical circuitry is operational or if rerouting can avoid said non-operational non-critical circuitry, generating a signal to reactivate said normal mode.

20. An apparatus for automatically returning a cardiac stimulator to a normal mode of operation from a backup mode of operation, said apparatus comprising:

means for determining whether selected memory locations contain valid information;

means for determining whether selected circuitry is operational; and means for generating a signal to reactivate said normal mode.

21. An apparatus for automatically returning a cardiac stimulator to a normal mode of operation from a backup mode of operation, said apparatus comprising:

means for storing information correlative to activation of said backup mode;

means for determining if a given number of recoveries have been attempted;

means for determining whether selected memory locations contain valid information;

means for determining whether programmed parameters correlative to said normal mode are valid;

means for determining whether selected critical circuitry is operational;

means for determining whether selected non-critical circuitry is operational; and means for generating a signal to reactivate said normal mode.

* * * * *